United States Patent [19]

Rosen et al.

[11] Patent Number: 4,943,628

[45] Date of Patent: Jul. 24, 1990

[54] HIV PEPTIDE-INDUCTED T CELL STIMULATION

[75] Inventors: Jonathan I. Rosen; John F. Warner, both of San Diego, Calif.

[73] Assignee: Ortho Pharmaceutical Corporation, Raritan, N.J.

[21] Appl. No.: 205,983

[22] Filed: Jun. 13, 1988

[51] Int. Cl.$^5$ .............................................. C07K 7/08
[52] U.S. Cl. .................................. 530/326; 514/14; 514/15; 514/17; 530/328; 530/330; 424/89
[58] Field of Search ................. 424/89; 530/326, 330, 530/328; 514/17, 14, 15; 435/5

[56] References Cited

PUBLICATIONS

Aids Research and Human Retroviruses, vol. 4, No. 3, 1988, Yourno et al., pp. 165–174.
Proc. Natl. Acad. Sci. U.S.A., vol. 84, pp. 2479–2483, Apr. 1987, Parker et al.
Journal of Virology, Feb. 1987, pp. 570–578, Modrow et al., Febs Letters, vol. 218, No. 2, 231–237, Jun. 1987, Steinberg et al.
Ratner, L. et al., (1985). Complete Nucleotide Sequence of the Aids Virus, HTLV-III, Nature 313: 277–284.
Putney, S. D. et al., (1988), HTLV-III/LAV–Neutralizing Antibodies to an E. Coli–Produced Fragment of the Virus Envelope, Science 234:1392–1395.
Lasky, L. A. et al., (1987). Delineation of a Region of the Human Immunodeficiency Virus Type 1 gp120 Glycoprotein Critical for Interaction with the CD4 Receptor, Cell 50:975–985.
Cease, K. B. et al., (1987), Helper T-Cell Antigenic Site Identification in the Acquired Immunodeficiency Syndrome Virus gp120 Envelope Protein and Induction of Immunity in Mice to the Native Protein Using a 16-Residue Synthetic Peptide, Proc. Natl. Acad. Sci., U.S.A., 84: 4249–4253.
Ho, D. D. et al., (1988) Second Conserved Domain of gp120 is Important for HIV Infectivity and Antibody Neutralization, Science 239: 1021–1023.
Milich, D. R. et al., (1987), Antibody Production to the Nucleocapsid and Envelope of the Hepatitis B Virus Primed by a Single Synthetic T Cell Site, Nature 329: 547–549.
Krohn, K. et al., (1988), Group Specific Helper T-Cell Response Towards HIV Requires Identification of Two Epitopes on the External Glycoprotein, IV International Conference on Aids, Abstract #1189.
Palker, T. J. et al., (1988), Bivalent Synthetic Peptide Inoculum Elicits High Titers of Neutralizing Antibodies to Human Immunodeficiency Virus (HIV) Isolates HTLV-III and HTLV-III$_{RF}$. IV International Conference on Aids, Abstract #1192.
Berzofsky, A. J. et al., (1988), An Immunodominant Epitope of HIV Envelope Recognized by Class I-MHC Restricted Murine Cytotoxic T Cells. IV International Conference on Aids, Abstract #2220.
Warner, J. F. et al., (1988), T Cell Reactive Epitopes from HIV GP120 IV International Conference on Aids, Abstract #2218.
DeLisi, C. and Berzofsky, J. A. (1985), T-Cell Antigenic Sites Tend to be Amphiphgathic Structures, Proc. Natl. Acad. Sci., U.S.A., 82: 7048–7052.

Primary Examiner—Lester L. Lee
Assistant Examiner—T. D. Wessendorf
Attorney, Agent, or Firm—Michael Stark

[57] ABSTRACT

The present invention provides peptides derived from HIV-1 which are capable of stimulating T cell proliferation. Such peptides are useful for immunizing human subjects against HIV infection.

1 Claim, 5 Drawing Sheets

FIG-4 ly, peptides possessing these characteristics are included in the scope of the present invention.

HIV PEPTIDE-INDUCTED T CELL STIMULATION

BACKGROUND OF THE INVENTION

HIV is the etiological agent of what is commonly known as Acquired Immunodeficiency Syndrome (AIDS). HIV is an RNA retrovirus that has been given different names over the past several years, such as human T-lymphotropic virus III (HTLV-III); lymphadenopathy-associated virus (LAV); or AIDS-associated retrovirus (ARV). At the present time, HIV is being referred to as HIV-1 in order to differentiate it from a related virus designated HIV-2 (or LAV-2). For the purposes of this disclosure, the presently accepted designation HIV will be used to designate any viral agent that causes AIDS.

A characteristic of AIDS is the inability of the host immune system to effectively control virus replication, despite high levels of virus-specific antibodies, a subset of which are capable of neutralizing HIV in vitro. Nonetheless, patients possessing these antibodies and low levels of cytotoxic T cells appear to eventually succumb to the disease. Therefore, a better understanding of the HIV-1 antigenic determinants and their recognition by immune effector mechanisms would expedite the development of effective preventative and therapeutic modalities against AIDS.

Studies of experimental animal and human antibody responses to HIV have progressed quite rapidly, whereas the examination of T cell responses has lagged because of technical constraints, e.g., availability of highly active effector cells and appropriate infected targets. In order to identify regions within the HIV-1 envelope protein sequence that are capable of simulating immune effectors, in particular, T cells, applicants synthesized and examined a series of overlapping synthetic peptides derived from the carboxy-half of the gp120 envelope glycoprotein. Several such peptides have been identified which are capable of stimulating T cell proliferation.

ABBREVIATIONS

| ABBREVIATIONS | |
|---|---|
| Amino Acid | One-Letter Symbol |
| Alanine | A |
| Arginine | R |
| Asparagine | N |
| Aspartic Acid | D |
| Asparagine or aspartic acid | B |
| Cysteine | C |
| Glutamine | Q |
| Glutamic acid | E |
| Glutamine or glutamic acid | Z |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

SUMMARY OF THE INVENTION

The present invention provides peptides derived from HIV-1 which are capable of stimulating T cell proliferation. Such peptides comprise a T cell epitope. Also provided are vaccines comprising the novel peptides, as well as methods for immunizing human subjects against HIV-1 infection.

DETAILED DESCRIPTION OF THE INVENTION

The present invention is based on a peptide derived from HIV-1 capable of stimulating T cell proliferation which comprises a T cell epitope. As used herein, "peptide" refers to a linear series of less than about 60 amino acid residues connected to one another by peptide bonds between the alpha-amino groups and carboxy groups of adjacent amino acid residues. The term "synthetic peptide" means a chemically derived chain of amino acid residues linked together by Peptide bonds that is free of naturally occuring proteins and fragments thereof. Additionally, analogs, fragments, chemical derivatives and pharmaceutically acceptable salts of the novel peptides provided herein are included within the scope of the term "peptide".

In one embodiment of the invention the Peptide comprises the amino acid residue sequence GNMRQ. In another embodiment of the invention the peptide comprises an amino acid residue sequence selected from the group of sequences consisting of GNMRQAHCNI and PEIVTHSFNC. In yet another embodiment of the invention the peptide comprises an amino acid residue sequence selected from the group of sequences consisting of
HGIRPVVSTQLLLNG,
SLAEEEVVIRSANFT,
DNAKTIIVQLNQSVE,
IIVQLNQSVEINCTR,
GRAFVTIGKIGNMRQ
TIGKIGNMRQAHCNI,
GNMRQAHCNISRAKW,
LREQFGNNKTIIFKQ, SSGGDPEIVTHSFNC,
PEIVTHSFNCGGEFF,
ITLPCRIKQIINMWQ,
RIKQIINMWQEVGKA,
WRSELYKYKVVKIEP and
YKYKVVKIEPLGVAP.

The present invention further provides peptides having the amino acid residue sequence:
HGIRPVVSTQLLLNG,
SLAEEEVVIRSANFT,
DNAKTIIVQLNQSVE,
IIVQLNQSVEINCTR,
GRAFVTIGKIGNMRQ
TIGKIGNMRQAHCNI,
GNMRQAHCNISRAKW,
LREQFGNNKTIIFKQ,
SSGGDPEIVTHSFNC,
PEIVTHSFNCGGEFF,
ITLPCRIKQIINMWQ,
RIKQIINMWQEVGKA,
WRSELYKYKVVKIEP and
YKYKVVKIEPLGVAP.

The one-letter symbols used to represent the amino acid residues in the peptides of the present invention are those symbols commonly used in the art. The term "analog" refers to any peptide having a substantially identical amino acid sequence to a peptide provided herein and in which one or more amino acids have been substituted with chemically similar amino acids. For instance, one polar amino acid, such as glycine or serine, may be substituted for another polar amino acid; or one acidic amino acid, such as aspartic acid may be substituted for another acidic amino acid, such as glutamic acid; or a basic amino acid, such as lysine, arginine or histidine may be substitued for another basic amino acid; or a non-polar amino acid, such as alanine, leucine or isoleucine may be substituted for another non-polar amino acid.

The term "analog" also means any peptide which has one or more amino acids deleted from or added to a peptide of the present invention but which still retains a substantial amino acid sequence homology to such peptide. A substantial sequence homology is any homology greater than 50%. The term "fragment" means any shorter version of the peptides identified herein having at least five amino acid residues, wherein the fragment is capable of stimulating T-cell proliferation.

The term "chemical derivative" means any peptide derived from a peptide of the present invention and in which one or more amino acids have been chemically derivatized by reaction of the functional side groups of the amino acids residues present in the peptide. Thus, a "chemical derivative" is a peptide that is derived from the sequences or peptides identified herein by one or more chemical steps. Such derivatized molecules include, for example, those molecules in which free amino groups have been derivatized to form amine hydrochlorides, p-toluene sulfonyl groups, carbobenzoxy groups, t-butyloxycarbonyl groups, thiourethane-type derivatives, trifluoroacetyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The peptides of the present invention may be prepared by any of the following known techniques. Conveniently, the peptides may be prepared using the solid-phase synthetic technique initially described by Merrifield, in J. Am. Chem. Soc. 85:2149–2154 (1963). Other peptide synthesis techniques may be found, for example, in M. Bodanszky et al., *Peptide Synthesis*, John Wiley & Sons, 2d Ed., (1976) as well as in other reference works known to those skilled in the art. A summary of peptide synthesis techniques may be found in J. Stuart and J. D. Young, *Solid Phase Peptide Synthesis*, Pierce Chemical Company, Rockford, Ill. (1984). The synthesis of peptides by solution methods may also be used, as described in *The Proteins*, Vol. II, 3d Ed., Neurath, H. et al., Eds., p. 105–237, Academic Press, New York, N.Y. (1976). Appropriate protective groups for use in such syntheses will be found in the above texts as well as in J .F. W. McOmie, *Protective Groups in Organic Chemistry*. Plenum Press, New York, N.Y. (1973). Of course, the present peptides may also be prepared by recombinant DNA techniques, although such methods are not preferred.

In general, these synthetic methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine. Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final peptide.

The peptides of the present invention may be linked to an additional sequence of amino acids by either or both the N-terminus and the C-terminus, wherein the additional sequences are from 1 to about 45 amino acids in length. Such additional amino acid sequences, or linker sequences, can be conveniently affixed to a detectable label or solid matrix, or carrier. Labels, solid matrices and carriers that can be used with peptides of the present invention are described below. Typical amino acid residues used for linking are tyrosine, cysteine, lysine, glutamic acid and aspartic acid, or the like.

Any peptide of the present invention may be used in the form of a pharmaceuticallylly acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

Vaccines are also provided which comprise an effective HIV-immunizing amount of a peptide of the present invention and a pharmaceutically acceptable carrier. The term "pharmaceutically acceptable" refers to a molecular entity or composition that does not produce an allergic or similar untoward reaction when administered to a human. In one embodiment of the invention the vaccine comprises at least two peptides.

The pharmaceutically acceptable carrier may take a wide variety of forms depending on the form of preparation desired for administration, e.g. sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g. suspensions, elixirs and solutions) or carriers such as starches, sugars, diluents, granulating agents, lubricants, binders, disintegrating agents, and the like in the case of oral solid preparations (e.g. powders, capsules and tablets). Controlled release forms may also be used. Because of their ease in administration, tablets and capsules represent the most advantageous oral dosage unit form, in which case solid pharmaceutical carriers are obviously employed. If, desired, tablets may be sugar coated or enteric coated by standard techniques.

Methods for immunizing a human subject against HIV infection are also provided which comprise administering to the human subject an effective immunizing amount of a vaccine of the present invention. For vaccines to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

The peptides provided herein may be operatively linked to an immunogenic carrier. As used herein, the term "operatively linked" means that the peptide and carrier protein are physically associated by a linking means that does not interfere with the ability of either of the linking groups to function as described. Because immunogenic carriers are typically proteins themselves, the techniques of protein conjugation or coupling through activated functional groups is particularly applicable. For review of those techniques, see Aurameas et al., Scand. J. Immunol., Vol. 8, Supp. 1, pp. 7–23 (1978). See, also, U.S. Pat. Nos. 4,493,795 and 4,671,958.

Useful immunogenic carriers are well known in the art and are generally large proteins. Exemplary of such carriers are keyhole limpet hemocyanin (KLH); edestine, thyroglobulin; albumins, such as bovine serum albumin (BSA) or human serum albumin (HSA); red blood cells, such as sheep erythrocytes (SRBC); tetanus toxoid; cholera toxoid; and polyamino acids, such as poly(d-lycine:d-glutamic acid) and the like.

The vaccine may also contain additional immunopotentiators, i.e., a molecular entity that stimulates the maturation, differentiation and function of B and/or T-lymphocytes. Immunopotentiators are well known in the art and include T-cell stimulating polypeptides such as those described in U.S. Pat. No. 4,426,324 and the C8-substituted guanine nucleosides described by Goodman et al., J. Immunol., 135:3284–3288 (1985) and U.S. Pat. No. 4,643,992.

The preparation of a vaccine that contains a peptide as an active ingredient is well understood in the art. Typically, such vaccines are prepared as injectibles, either as liquid solutions or suspensions; solid forms suitable for solution in or suspension in liquid prior to injection may also be prepared. The preparation may also be emulsified.

The vaccines may conventionally be administered parenterally, by either intravenous, subcutaneous, or intramuscular injection. Additional formulations which are suitable for other modes of administration include suppositories and, in some cases, oral formulations. For suppositories, traditional binders and carriers may include, for example, polyalkylene glycols or triglycerides. Oral formulations include such normally employed excipients as, for example, pharmaceutical grades of mannitol, lactose, starch, magnesium stearate, sodium saccharin, cellulose, magnesium carbonate and the like. Compositions may take the form of solutions, suspensions, tablets, pills, capsules, sustained release formulations or powders.

The vaccines may be administered in a manner compatible with the dosage formulation, and in such amount as will be therapeutically effective and immunogenic. The quantity to be administered depends on the subject to the treated, capacity of the subject's immune system to synthesize the antibodies and the degree of protection desired. Precise amounts of active ingredient required to be administered depend on the judgment of the practitioner and are peculiar to each individual.

The vaccine may also include an adjuvant as part of the excipient. Adjuvants such as complete Freund's adjuvant (CFA) or, incomplete Freund's adjuvant (IFA) for use in laboratory animals are well known in the art. Pharmaceutically-acceptable adjuvants such as alum may also be used.

The following experiments are provided for the purpose of illustrating the subject invention but in no way limit its scope, which is defined by the claims appended hereto.

MATERIALS AND METHODS

Mice: Inbred female mice were obtained from the Charles River Breeding Laboratories (Wilmington, Mass.). Mice 6–12 weeks of age of the following strains were used: C57BL/6 (B6); DBA/2; C3H/He; (C57BL/6×DBA/2)F$_1$ (B6D2F1); (C57BL/6×C3H)F$_1$ (B6C3F1); and (BALB/c×C57BL/6)F$_1$ (CB6F1): BALB/c and B6 mice were also obtained from MTS Laboratories (San Diego, Calif.). Peptide Synthesis: Overlapping synthetic peptides, each 15 amino acids in length (15-mers) and containing 10 amino acids in common with the preceding peptide, were synthesized using the method of Houghton et al. (Houghten, R. A. (1985) Proc. Natl. Acad. Sci. U.S.A. 82:5131-5135). All peptides were more than 50% pure as determined by analytical HPLC and amino acid analysis (Beckman System 6300).

Immunization Protocol: Mice were injected in two lateral sites at the base of the tail (tailbase) (Corradin et al. (1977) J. Immunol. 119: 1048-1053) with various synthetic peptides emulsified in complete Freund's adjuvant (CFA). Control mice were injected with CFA alone. Peptides were injected at a dose of 25-50 ug/50ul at two sites. Mice were sacrificed 7-8 days later and the periarterial and inguinal lymph nodes removed and placed in cold Hank's balanced salt solution (HBSS).

Lymphocyte Proliferation Assay: Lymph nodes obtained from immunized mice were minced in HBSS and passaged through sterile nylon-mesh screen (Tetko, Monterey Park, Calif.) to remove debris and obtain single cell suspensions. The cells were washed two times in HBSS and resuspended at $3 \times 10^6$ cells/ml in RPMI 1640 medium supplemented with 5% heat-inactivated fetal bovine serum (HIFBS) (Hyclone Laboratories, Provo, Utah), L-glutamine (1%), sodium pyruvate (1%), non-essential amino acids (1%), 2-8 mercaptoethanol ($5 \times 10^{-5}$M), and gentamycin (20 ug/ml). Cell viability was generally greater than 95% as visualized by trypan blue staining. Primed lymph node cells ($3 \times 10^5$/well) were added to flat-bottom microtiter plate (Costar) wells containing previously titrated amounts of peptide or inactivated HIV-1 (Hillcrest Biologicals, Inc., Cypress, Calif.) in a total volume of 200 ul. The plates were incubated at 37° C. in 5% $CO_2$ in air for 5-6 days. The cultures were pulsed during the last 16 hrs with $^3$H-thymidine (2.0 mCi/mM, New England Nuclear, Billerica, Mass.), individual wells harvested using a PHD cell harvester (Cambridge Technology, Cambridge, Mass.) and the radionucleotide incorporation measured in a Beckman LS 1800 scintillation counter. The level of $^3$H-thymidine incorporation was calculated as the simulation index (S.I.)=CPM of primed cells + peptide or inactivated HIV-1/CPM of primed cells alone.

Human CD4+ T cells were stimulated with the peptides provided herein by the following procedure; blood was obtained from HIV-1 seropositive patients and the peripheral blood mononuclear cells (PBM) isolated following ficoll-hypaque gradient centrifugation. The CD4+ cells were separated by panning of PBM on petri dishes previously coated with OKT4 monoclonal antibody (Ortho Pharmaceutical Corp., Raritan, N.J.). The separated CD4+ cells were then cultured with the peptides and $^3$H-thymidine incorporation determined as described above.

T cell Deoletion: Primed lymph node cells were treated with either anti-Lyt 1 (1:20), anti-LYt 2.1/2.2 (1:20) (Accurate Chemical, San Diego Calif.), or anti-L3T4 (1:100, RL=172.4) (kindly provided by Dr. M. Bevan, Scripps Clinic and Research Foundation, La Jolla, Calif.) monoclonal antibodies at 4° C. for 45 min. The treated cells were centrifuged, resuspended in rabbit complement (1:10, Low-tox, Accurate Chemical, San Diego, Calif.) and incubated at 37° C. for 45 min. Cells were washed three times in HBSS with 2% HIFBS, resuspended at $3 \times 10^6$ cells/ml in RPMI 1640 supplemented medium (above), and 100 μul added to respective microtiter wells for the proliferation assay.

Antibody Induction and Assay: B6D2F1 mice were immunized subcutaneously with 50 μg of free peptides emulsified in incomplete Freund's adjuvant (IFA) and the animals boosted twice at monthly intervals with the same peptides in IFA. Collected sera were analyzed by ELISA using the respective peptide immobilized on solid phase microtiter plates (Costar). The specificity of the antibody binding was established by competing with homologous peptide. Final antibody titers were determined as the dilution at which the reactivity was twice background.

RESULTS

Peptide sequences: Since the HIV gp120 envelope protein is expressed on the surface of HIV-infected cells, regions within gp120 are likely to provide determinants necessary for activating a cellular immune response. Applicants synthesized peptides (15-mers) with overlapping sequences (10 amino acids) which extend across the carboxy-half of gp120 (i.e., amino acids 256 to 519). The amino acid sequences were based on that of the HT published sequence (Ratner et al. (1985) Nature 313:277-284 ). The pverlapping gp120 peptide sequences are shown in Table I.

TABLE I

| CARBOXY-TERMINAL HIV GP120 PEPTIDES |
|---|
| C42 HGIRPVVSTQLLLNG |
|     C43 VVSTQLLLNGSLAEE |
|         C44 LLLNGSLAEEEVVIR |
|             C45 SLAEEEVVIRSANFT |
|                 C46 EVVIRSANFTDNAKT |
|                     C47 SANFTDNAKTIIVQL |
|                         C48 DNAKTIIVQLNQSVE |
|                             C49 IIVQLNQSVEINCTR |
|                                 C50 NQSVEINCTRPNNNT |
|                                     C51 INCTRPNNNTRKSIR |
| C52 PNNNTRKSIRIQRGP |
|     C53 RKSIRIQRGPGRAFV |
|         C54 IQRGPGRAFVTIGKI |
|             C55 GRAFVTIGKIGNMRQ |
|                 C56 TIGKIGNMRQAHCNI |
|                     C57 GNMRQAHCNISRAKW |
|                         C58 AHCNISRAKWNNTLK |
|                             C59 SRAKWNNTLKQIDSK |
|                                 C60 NNTLKQIDSKLREQF |
|                                     C61 QIDSKLREQFGNNKT |

TABLE I-continued
CARBOXY-TERMINAL HIV GP120 PEPTIDES

```
C62  LREQFGNNKTIIFKQ
     C63  GNNKTIIFKQSSGGD
          C64  IIFKQSSGGDPEIVT
               C65  SSGGDPEIVTHSFNC
                    C66  PEIVTHSFNCGGEFF
                         C67  HSFNCGGEFFYCNST
                              C68  GGEFFYCNSTQLFNS
                                   C69  YCNSTQLFNSTWFNS
                                        C70  QLFNSTWFNSTWSTK
                                             C71  TWFNSTWSTKGSNNT

C72  TWSTKGSNNTEGSDT
     C73  GSNNTEGSDTITLPC
          C74  EGSDTITLPCRIKQI
               C75  ITLPCRIKQIINMWQ
                    C76  RIKQIINMWQEVGKA
                         C77  INMWQEVGKAMYAPP
                              C78  EVGKAMYAPPISGQI
                                   G79  MYAPPISGQIRCSSN
                                        G80  ISGQIRCSSNITGLL
                                             G81  RCSSNITGLLLTRDG

C82  ITGLLLTRDGGNSNN
     C83  LTRDGGNSNNESEIF
          C84  GNSNNESEIFRPGGG
               C85  ESEIFRPGGGDMRDN
                    C86  RPGGGDMRDNWRSEL
                         C87  DMRDNWRSELYKYKV
                              C88  WRSELYKYKVVKIEP
                                   C89  YKYKVVKIEPLGVAP
                                        C90  VKIEPLGVAPTKAKR
                                             C91  LGVAPTKAKRRVVQR
                                                  C92  TKAKRRVVQREKRA
```

Figure 1:
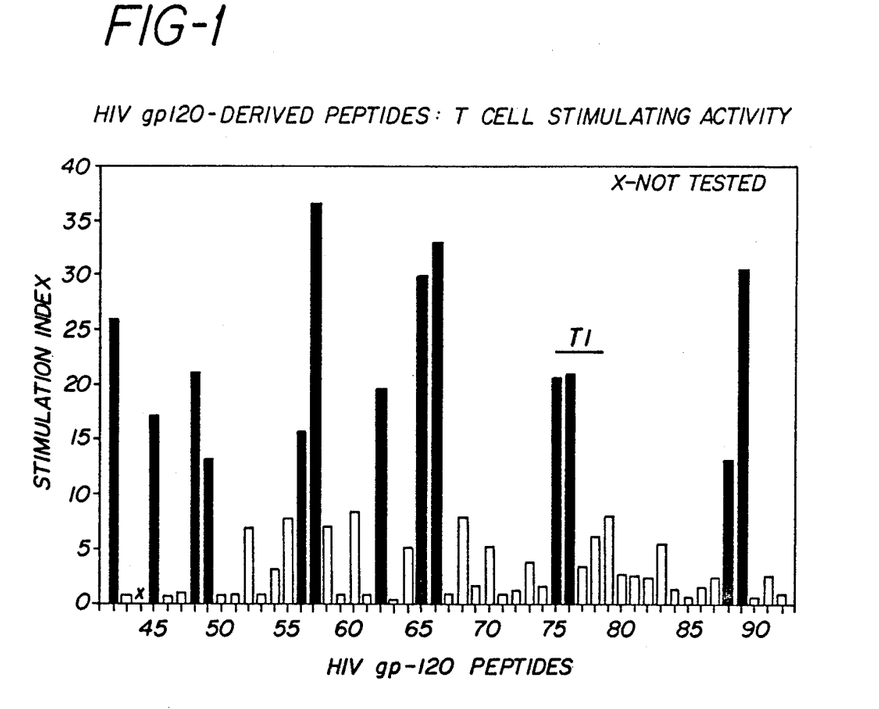
FIG. 1—All peptides were assayed for stimulatory activity in the mouse model. The eight highly reactive regions (stimulation index greater than 10) are shown in black.

Peptide-induced proliferation of primed lymph node cells: To determine whether peptides derived from the HIV-1 gp120 sequence can sensitize (prime) lymphocytes, in particular T cells, to later recognize structures on the intact virus, applicants examined the ability of individual peptides to sensitize lymphocytes in vivo such that subsequent in vitro exposure to the homologous peptide would induce cell proliferation, i.e., $^3$H-thymidine incorporation. B6D2F$_1$ mice were immunized with individual peptides and the lymph node cells restimulated in vitro seven days later with titrated amounts of homologous peptide. These cultures were then continued for 5-7 days and the proliferative activity measured. A number of peptides were capable of inducing significant cell proliferation (FIG. 1). In most cases, at least one overlapping neighbor peptide stimulated significant responses, (e.g., peptides C48-49, C56-57, C65-66, C75-76, and C88-89). Certain individual peptides were also capable of stimulating proliferation (e.g., peptides C42, C45, and C62). There appeared to be several regions of stimulatory activity, although the sequences do not appear to be strictly associated with amphipathic alpha-helical configuration. However, peptides C48 C66 and C76 exhibit hydrophobic moments which indicate significant amphiphathic structure. Interestingly, adjacent peptides, e.g. C49 and C65, which are equally stimulatory do not have significant amphipathic characteristics.

Figure 2:
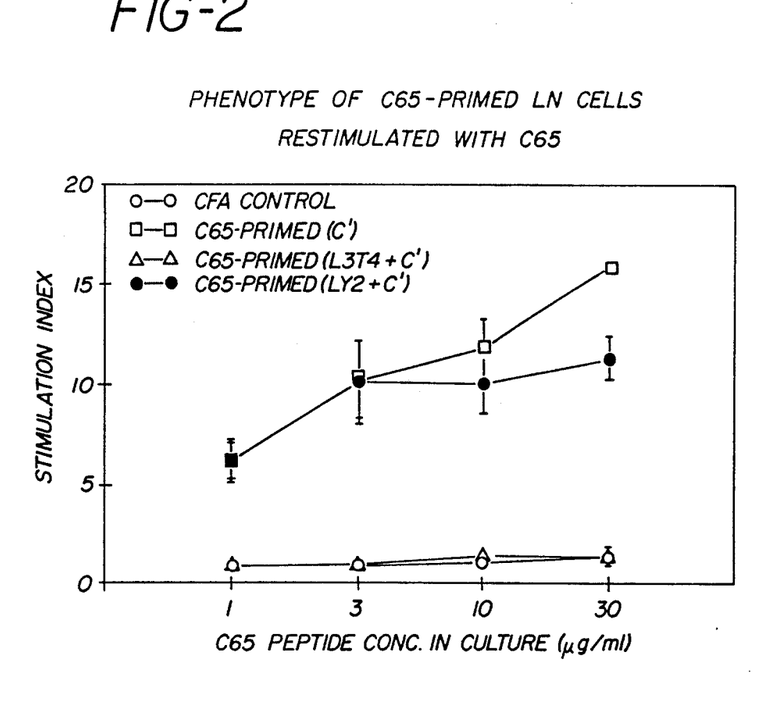
FIG. 2—Anti-L3T4 + complement completely abolished stimulatory activity for peptide C65. The activity of all other stimulatory peptides was equally inhibited by anti-L3T4. This indicates that the cells responsible for stimulation are of the T-helper phenotype.

Peptide-activated proliferating cells are T cells: To determine the phenotypic nature of the proliferating cells, mice were immunized with peptides previously shown (FIG. 1) to induce significant $^3$H-thymidine incorporation. The in vivo sensitized lymph node cells were treated with monoclonal antibodies (mAb) directed against major T cell determinants (i.e., L3T4 and Lyt 2) plus complement (C') in order to deplete selected T cell populations. The depleted cell populations were subsequently re-stimulated in vitro with homologous peptides in order to determine which population of cells was still capable of proliferating. FIG. 2 depicts the results of an experiment in which B6D2F$_1$ mice were immunized with the C65 pep tide, the primed lymph node cells treated with the respective mAb plus C', and the treated cells stimulated in vitro with the C65 peptide. Lymph node cells treated with anti-L3T4 +C', i.e., depleted of L3T4+ cells, no longer exhibited proliferative activity compared to C'-treated control cultures. On the other hand, cells treated with anti-Lyt 2, i.e., depleted of Lyt 2+ cells, showed little reduction in proliferation and in some experiments, anti-Lyt 2 treatment augmented responses. Cell populations stimulated with other peptides, i.e., C42, C45, C48, C49, C56, C57, C62, C66, C75, C88, and C89, also did not exhibit proliferative activity following treatment with anti-L3T4, but did following anti-Lyt 2 treatment. In addition, proliferative responses of cells treated with anti-Lyt 1.1/1.2 were abrogated compared to controls. Therefore, it appears that the peptide-induced responses obtained in B6D2F$_1$ mice are due to activation of T cells with the L3T4+ (helper/inducer) phenotype.

Correlation between peotide-induced antibody production and peptides with T cell stimulating determinants: To examine the ability of non-conjugated (free) peptides to elicit antibody formation in mice as well as determine the influence on antibody production of peptides possessing T cell-stimulating determinants, B6D2F$_1$ mice were immunized with different free peptides in CFA, boosted twice with homologous peptide at monthly intervals and the levels of peptide-specific antibody determined one week after the final immunization. A number of peptides were found to elicit significant peptide-specific antibody titers and were ranked accordingly (Table II).

TABLE II

Comparison of T Cell Priming and Antibody Production Induced by HIV Peptides

| PEP-TIDE | SEQUENCE | T CELL STIMU-LATION | ANTIBODY TITER* |
|---|---|---|---|
| C57 | GNMRQAGCNISRAKW | +++ | 100,000/50,000 |
| C65 | SSGGDPEIVTHSGNC | +++ | 50,000/100,000 |
| C66 | PEIVTHSFNCGGEFF | +++ | 25,000/12,000 |
| C89 | YKYKVVKIEPLGVAP | +++ | 25,000/1,600 |
| C45 | SLAEEEVVIRSANFT | ++ | 25,000/3,000 |
| C56 | TIGKIGNMRQAHCNI | ++ | 25,000 |
| C60 | NNTLKQICSKLREQF | + | 6,000/12,000 |
| C78 | EVGKAMYAPPISGQI | + | 6,000 |
| C79 | MYAPPISGQIRCSSN | + | 400/1,600 |
| C64 | IIFKQSSGGDPEIVT | ± | <10 |
| C74 | EGSDTITLPCRIKQI | − | 400/200 |
| C54 | IQRGPGRAFVTIGKI | − | <10/<10 |

*Titers obtained from two individual mice

There appeared to be a correlation between peptides capable of inducing significant antibody production and their ability to stimulate T cells proliferation (Table II, FIG. 1). This indicates that certain peptides possess both T cell and B cell activating determinants and is in agreement with the helper T cell phenotype of the peptide-stimulated cells previously described (FIG. 2).

Figure 3:
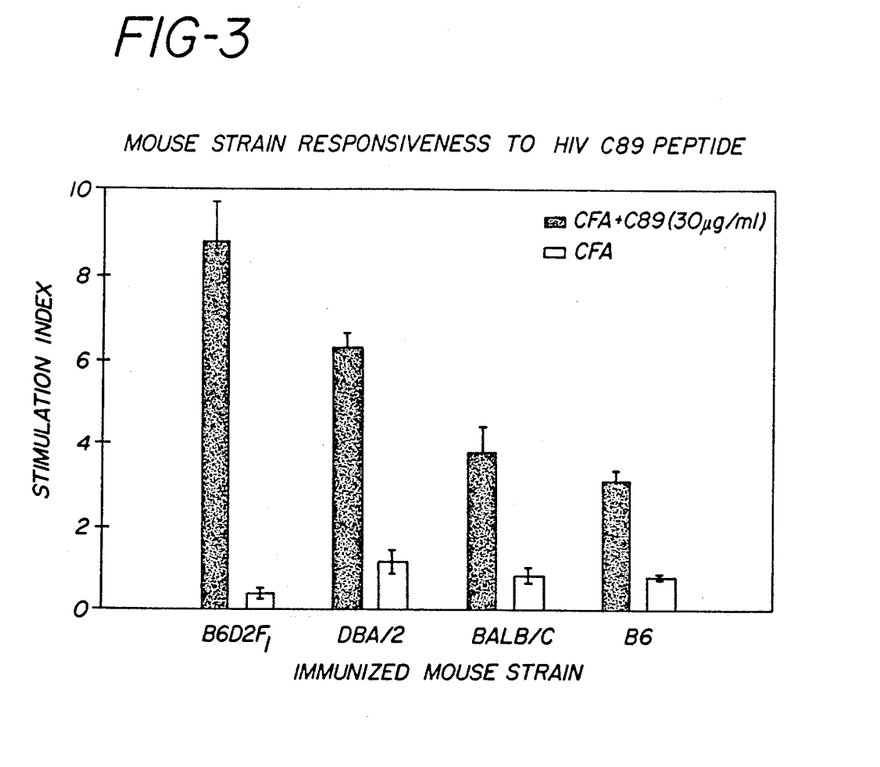
FIG. 3—different mouse strains were immunized with peptide C89 in complete Freund's adjuvant. Lymphocytes from the immunized animals were then assayed for peptide dependent stimulation. As can be seen, T-cells from the F1 strain (B6D2F1) recognized peptide better than either parental strain.

Peptide-induced proliferation varies with regard to mouse strain: Inbred strains of mice with different H-2 haplotypes were immunized with certain peptides in order to determine the influence of strain variation on anti-peptide responsiveness B6D2F$_1$, DBA/2, B6, and BALB/c and mice were immunized with the C89 peptide, the lymph node cells cultured 7 days later with homologous peptide and the proliferative activity analyzed. The F$_1$ hybrid mice showed significantly better responses with respect to the individual parental strains, i.e., B6 and DBA/2 (FIG. 3). Moreover, DBA/2 (H-2$^d$) mice appeared to respond better than did H-2 compatible BALB/c (H-2$^d$) mice. In these experiments, F$_1$ hybrid mice, in general, appeared to respond better than their parental strains. These results indicate that the level of peptide-induced stimulation can be influenced considerably by the genetic makeup of the experimental mouse strains employed and point to the usefulness of F$_1$ hybrid mice as an initial model for screening large numbers of peptides.

Figure 4:
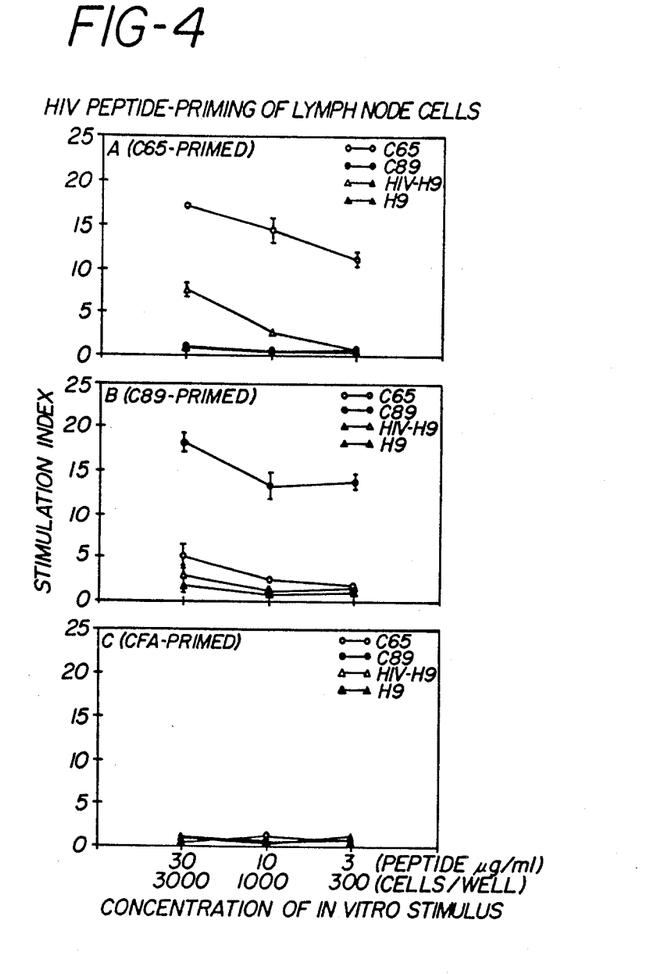
FIG. 4—Two stimulatory Peptides were assayed for their ability to Prime cells to native HIV. Lymphocytes from mice immunized with peptide C65 were stimulated in vitro by HIV-infected cells. However, peptide C89 primed lymphocytes did not recognize native HIV.

Peptide-primed T cells recognize HIV-1 infected cells: To determine the ability of peptide-primed lymph node T cells to recognize virally-infected cells, B6D2F$_1$ mice were immunized with either the C65 or C89 peptides. The sensitized lymph node cells were stimulated 7 days later with homologous peptide, heterologous peptide, or with HIV-1 infected and non-infected H9 cells. The cultures were then assayed 5-6 days later for proliferative activity. Lymph node cells obtained from mice immunized with the C65 peptide responded after in vitro stimulation with the homologous C65 peptide, but not with the heterologous C89 peptide (FIG. 4, panel A). On the other hand, C89-primed cells exhibited specificity for the C89 peptide with negligible activity against C65 (FIG. 4, panel B). Most interesting, however, was the finding that C65-primed T cells responded to HIV-1 infected H9 cells compared to H9 non-infected cells (FIG. 4, panel A). Reactivity to virally-infected cells appeared to be a property of C65-primed T cells since C89-primed cells showed no reactivity to either HIV-1 infected H9 or non-infected H9 cells (FIG. 4, panel B). Cells from mice immunized with CFA alone showed no stimulation with either the peptides or infected/non-infected H9 cells. As a note, lymph node cells obtained from mice immunized with inactivated purified HIV-1 did not proliferate upon exposure to the gp120-derived peptides, but were stimulated by inactivated virus and peptides derived from core-region protein sequences. The inactivated viral preparation was found to have negligible amounts of gp120, thereby not capable of sensitizing cells to the envelope determinants. Therefore, the experiments described above were performed with HIV-infected cells which expressed gp120 on their surface. H9 and HIV-infected H9 cells were titrated to suboptimal stimulation levels in order to prevent primary responses against zenogenic determinants present on the human H9 cells. Although both peptides were capable of inducing significant peptide-specific T cell stimulation, only the C65-primed cells were able to recognize determinants expressed by HIV-1-infected H9 cells.

Figure 5:
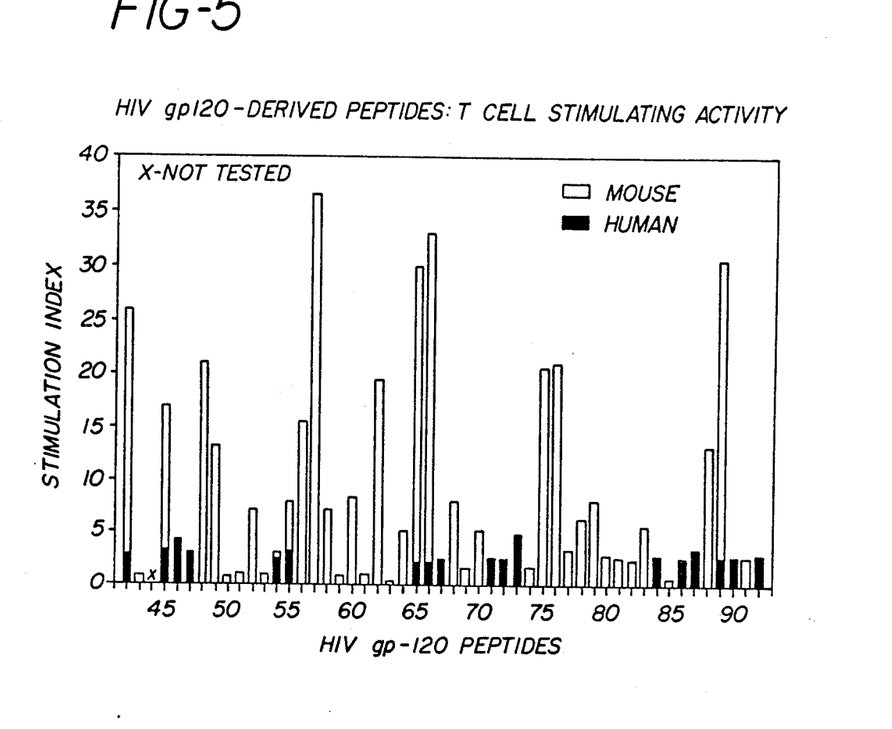
FIG. 5—Peptides capable of priming mouse T-cell responses were compared to those capable of stimulating human T-cells. Peptides from four of the stimulatory regions demonstrated activity in both systems.

Comparison of human (AIDS patient) and murine T cell responses to gp120 carboxy-terminal peptides: To determine whether murine and human T cells are able to respond against HIV-derived synthetic peptides and if so, whether the same or different peptides are recognized, the ability of AIDS/ARC patient CD4+ T cells to recognize this same panel of gp120 peptides was studied. A comparison was made between peptides recognized by T cells obtained from peptide-immunized mice and those peptides recognized by CD4+ T cells obtained from HIV-1 seropositive patients. A number of peptides, i.e., C42, C45, C65, C66 and C89, were stimulatory for both the human and murine cells (FIG. 5). Certain peptides were clearly not stimulatory for human patient cells but were reactive with murine cells and vice versa. However, there appeared to be similar regions of reactivity between the human and murine responses, particularly in regions including peptides C42-C49, C54-C57, C65-C66, and C84-C90.

Discussion

The present invention provides peptides with amino acid sequences derived from the carboxy-terminal region of gp120. Since this region may be involved in post-binding events during virus penetration (Ho et al. 1988 Science 239:1021–1023), such amino acid sequences provide important sites for antibody neutralization (Ho, et al. and Putney et al. (1986) Science 234:1392–1395), and contains a CD4 binding domain (Lasky et al. (1987) Cell 50:975–985).

The synthetic peptides provided herein are advantageous in delineating particular regions of gp120 which activate T cell as well as B cell responses. These exposed 'intermediate' determinants may be vital for viral penetration and infectivity, but are exposed for perhaps too short a period of time to allow for effective induction of an immune response, although long enough for recognition by previously activated immune mechanisms.

The current concept for antigen presentation and T cell activation suggests that foreign molecules are processed by antigen presenting cells, e.g., macrophages, B cells, etc., and dissociated into short peptide fragments. The peptides then associate with class I and class II MHC molecules to form an immunogenic antigen complex for induction of cytotoxic and helper T cells, respectively. The use of synthetic peptides as antigens may simply by-pass certain processing steps, with the peptides still capable of effecting immunological responses.

Applicants have identified a number of overlapping peptides which define regions within gp120 (carboxy-terminus) and which are capable of stimulating murine T cells. One of these regions, i.e., peptides C75-C79, corresponds to the T1 peptide described by Cease et al. (1987 Proc. Natl. Acad. Sci. U.S.A. 84:4249-4253) which also induced cell proliferation in a murine system. In addition, peptides C42-C45 correspond to the C21E peptide described by Ho et al. (1988 Science 239:1021-1023) which when conjugated to a carrier protein (i.e., keyhole limpet hemocyanin) elicited rabbit antibodies capable of binding to gp120 and neutralizing HIV infectivity as a post viral-binding event. Finally, the region described by Lasky et al. (1987 Cell 50:975-985) as a CD4 binding site (overlapping peptides C75-C82) stimulates murine lymphocytes, but shows no reactivity with human patient lymphocytes. Although this may be simply due to inherent differences between the abilities of the mouse and human immune effectors to recognize these peptides, it is also possible that this region is unavailable in humans due to its very strong interaction with CD4.

It is noteworthy that peptides which induced significant T cell proliferative responses appeared to activate only cells of the helper/inducer T cell subset, i.e., L3T4+). This finding was corroborated by the correlation between peptides which elicited increased antibody responses and those capable of inducing T cell proliferation (Table II, FIG. 1). The possibility exists that these peptides were presented in a context which caused them to preferentially associate with class II rather than class I MHC molecules and therefore, only helper T cells were activated. Nonetheless, the use of these peptides clearly allows for the identification of both potential T and B cell epitopes as has been described for the hepatitis B viral model (Millich et al. (1987) Nature 329:547-549). These peptides provide a basis for a vaccine by combining effective T cell activating sites with neutralizing B cell determinants to produce highly immunogenic molecules eliciting effective memory responses to the native virus.

Experiments using the C65 peptide (FIG. 5) indicate that the peptides of the subject invention prime T cells which are capable of recognizing intact viral proteins expressed on the surface of infected cells. The fact that certain peptides can induce significant and anti-peptide responses does not necessarily indicate that the same peptides can activate T cells which recognize intact viral molecules. This is illustrated by the inability of the C89 peptide-primed cells to recognize HIV-H9 cells. Since our inactivated viral preparation lacked sufficient gp120 to prime T cells, we employed HIV-infected H9 cells which had been titrated extensively in order to avoid primary zenogenic stimulation of murine T cells. The results indicate that peptide-primed, i.e., C65 peptide, lymph node T cells specifically recognized determinants presented only on HIV-infected H9 cells. However, it should be kept in mind that these experiments were performed with MHC incompatible responder-stimulator cell combinations.

The finding that certain peptides stimulated murine L3T4+ cells as well as human HIV-1 seropositive CD4+ T cells may provide some relevance for using the murine model as a preliminary screening tool. Individual peptides which stimulated murine T cells do not necessarily show an absolute correlation with those peptides capable of stimulating AIDS patient CD4+ T cells; however, they do appear to identify regions of similarity. We currently are unable to evaluate the degree to which the pathology of HIV-1 infection has influenced the anti-peptide responses detected with patient cells. Thus, differences between the murine and human responses could be due to a lack of equivalent recognition structures for these peptides between the species or the fact that the AIDS patient lymphoid cells have been comprised and are incapable of responding to certain peptides.

What is claimed is:
1. A peptide selected from the group consisting of:
HGIRPVVSTQLLLNG,
SLAEEEVVIRSANFT,
DNAKTIIVQLNQSVE,
IIVQLNQSVEINCTR,
GRAFVTIGKIGNMRQ,
TIGKIGNMRQAHCNI,
GNMRQAHCNISRAKW,
LREQFGNNKTIIFKQ,
SSGGDPEIVTHSFNC
PEIVTHSFNCGGEFF,
ITLPCRIKQIINMWQ,
RIKQIINMWQEVGKA,
WRSELYKYKVVKIEP, and
YKYKVVKIEPLGVAP.

* * * * *